United States Patent
Price et al.

(10) Patent No.: US 9,066,788 B2
(45) Date of Patent: Jun. 30, 2015

(54) ORTHOSIS

(76) Inventors: Stephen A. Price, Tampa, FL (US);
Mary P. Price, Tampa, FL (US)

( * ) Notice: Subject to any disclaimer, the term of this patent is extended or adjusted under 35 U.S.C. 154(b) by 497 days.

(21) Appl. No.: 12/559,111

(22) Filed: Sep. 14, 2009

(65) Prior Publication Data

US 2011/0066095 A1  Mar. 17, 2011

(51) Int. Cl.
| | |
|---|---|
| *A61F 5/00* | (2006.01) |
| *A63B 21/02* | (2006.01) |
| *A61F 5/01* | (2006.01) |
| *A61F 5/058* | (2006.01) |
| *A63B 21/00* | (2006.01) |
| *A63B 21/055* | (2006.01) |
| *A63B 23/035* | (2006.01) |

(52) U.S. Cl.
CPC ............. *A61F 5/0106* (2013.01); *A61F 5/0104* (2013.01); *A61F 5/0102* (2013.01); *A63B 21/1446* (2013.01); *A63B 21/02* (2013.01); *A63B 21/1403* (2013.01); *A63B 21/055* (2013.01); *A63B 23/035* (2013.01); *A61F 5/0118* (2013.01); *A61F 5/05841* (2013.01)

(58) Field of Classification Search
CPC ........... A61F 5/00; A61F 5/01; A61F 5/0102; A61F 5/0104; A61F 5/0106; A61F 5/0118; A63B 21/00; A63B 21/002; A63B 21/0023; A63B 21/02; A63B 21/055; A63B 21/0552; A63B 21/0555; A63B 21/14; A63B 21/1403; A63B 21/1423; A63B 21/1434; A63B 21/1446; A63B 21/1449; A63B 21/1484; A63B 23/00; A63B 23/035; A63B 23/03508; A63B 23/04; A63B 23/0494; A63B 23/12; A63B 23/1281

USPC ............ 602/23, 26, 60–63; 128/882; 482/91, 482/105, 121, 122, 124, 148

See application file for complete search history.

(56) References Cited

U.S. PATENT DOCUMENTS

| | | | | |
|---|---|---|---|---|
| 3,473,527 A | * | 10/1969 | Spiro | 602/26 |
| 3,703,171 A | * | 11/1972 | Schiavitto | 602/26 |
| 4,986,263 A | * | 1/1991 | Dickerson et al. | 602/26 |
| 5,397,296 A | | 3/1995 | Sydor et al. | |
| 6,261,253 B1 | | 7/2001 | Katzin | |
| 6,656,097 B2 | * | 12/2003 | Karecki | 482/148 |
| 6,773,411 B1 | * | 8/2004 | Alvarez | 602/27 |
| 6,923,780 B2 | | 8/2005 | Price et al. | |
| 7,163,519 B2 | | 1/2007 | Price et al. | |
| 2005/0038367 A1 | * | 2/2005 | McCormick et al. | 602/26 |
| 2009/0320299 A1 | * | 12/2009 | Kuhn et al. | 30/169 |

* cited by examiner

*Primary Examiner* — Alireza Nia
*Assistant Examiner* — Keri J Nelson
(74) *Attorney, Agent, or Firm* — Dale J. Ream

(57) ABSTRACT

An orthosis comprising a dynamic, flexible, elastic stiffener that is configured to extend across a joint. The stiffener is configured to extend across a joint in a first configuration, wherein the stiffener is preferably substantially planar, and a second configuration when a patient's muscle is under contraction such that the stiffener allows some joint movement but resists flexion of the joint to impede joint movement. The stiffener rebounds to its first configuration after the muscle contraction has terminated. The orthosis may be used to impede the movement of any joint, including a wrist joint and finger joints, an elbow joint, a knee joint, and an ankle joint and toe joints. Preferably, the flexible stiffener is made from a heat treated and tempered spring steel so that is has desirable dynamic and elastic properties.

1 Claim, 11 Drawing Sheets

ORTHOSIS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present application is directed to an orthosis and, more specifically, to an orthosis having a flexible stiffener.

2. Description of Related Art

Patients that have neurological disorders such as cerebral palsy and multiple sclerosis, muscular disorders, stroke victims, or persons with spinal cord injuries often uncontrollably contract their joints in flexion, which can cause the patients to lose range of motion in their joints. Common joints that are affected by patients having these conditions include wrist joints and finger joints, foot, toe, and ankle joints, hip joints, elbow joints, and knee joints. In an attempt to treat or otherwise alleviate the potential loss of range of motion due to conditions like those set forth above, doctors and physical therapists often secure an orthosis or splint across the affected joint to prevent uncontrollable flexion of the joint by stretching the joint to a desired position. The orthosis may be moved to a series of desired positions to stretch the joint and hopefully prevent a loss of range of motion.

Many different types of orthoses have been developed that stretch joints to a desired position thereby preventing patients wearing the orthoses from uncontrollably contracting their joints in flexion. For example, U.S. Pat. No. 6,261,253 to Katzin discloses a hand orthosis that limits finger and wrist flexion with a steel stiffener that provides a static resistance to the user. The stiffener is plastically deformed into the desired position to conform to the shape of the joint and surrounding limbs. However, the stiffener is made of material such that it will resist forces to which it is normally subjected when worn by a patient. That is, during contracture, the patient is unable to move the stiffener during use such that the stiffener provides a static resistance to the joint. While this property is useful in many circumstances, the needs of certain patients require a different type of stiffener.

The assignee of the present application has also developed knee and elbow orthoses for treatment of undesirable flexural contractions of those joints. These knee and elbow orthoses utilize goniometers which are adjustable to allow a certain degree of joint movement. For example, if zero degrees represents the angle of a patient's arm or leg when it is straight, then the goniometer can be adjusted so that the patient can only move his or her arm or leg a predetermined number of degrees freely within the range of movement allowed by the goniometer. For some patients it is undesirable to use an orthosis that allows this type of movement, even if it is only within a certain range.

Thus, while orthoses have been used to treat or alleviate the symptoms of uncontrollable joint flexion, there is a need for the type of orthosis that is shown and described in the present application.

BRIEF SUMMARY OF THE INVENTION

The present application is directed toward an orthosis having a dynamic flexible stiffener that is configured to extend across a joint and impede joint movement caused by muscle contractions by resisting flexing but allowing some movement in the joint. The stiffener is elastic so that it rebounds to its original form after flexing due to movement of the joint. The orthosis may be used to impede the movement of any joint. Preferably, however, the orthosis is designed to impede movement of the wrist and finger joints, the elbow joint, the knee joint, the hip joint, or the ankle and toe joints by having the flexible stiffener extend across the respective joint. Because the stiffener is elastic it allows joint movement, while constantly providing resistance to the movement until the joint returns to its original position. For certain patients, the stiffener of the present invention is better than conventional orthoses at preventing loss of range of motion due to its dynamic properties. It is believed that the ability of the stiffener of the present invention to provide a patient's joint with a range of motion, while resisting that joint motion, assists in preventing degeneration of the joint and the muscles connected to it. This feature is not present in the conventional orthoses described above, which cannot be moved by the patient.

In one embodiment, the orthosis extends across a wrist joint and finger joints for impeding movement of the wrist joint and finger joints caused by muscle contractions. The orthosis has a flexible dynamic stiffener that extends across the wrist and finger joints and a cover that encloses the stiffener. The cover is preferably secured to the arm and hand of a patient via a wrist strap and at least one hand strap. Preferably, forearm and hand stabilizers are joined to the stiffener and bent upward with respect to the stiffener to form a channel for retaining a forearm and hand.

In another embodiment, the orthosis is designed to impede movement of an ankle joint and toe joints caused by muscle contractions. The orthosis includes an L-shaped splint with one end positioned adjacent a posterior lower leg and an opposite heel end positioned underneath a heel. A flexible dynamic stiffener is joined to the heel end of the splint and extends from the splint to the toes of a patient wearing the orthosis. Preferably, a fabric boot is secured to the splint and the stiffener to secure them to the patient's leg and foot. Preferably, the boot has a leg strap and a foot strap for securing the orthosis to the patient.

Another embodiment of orthosis impedes movement of a patient's elbow joint caused by muscle contraction. The orthosis has a tubular brace that receives an arm of the patient and extends across the elbow joint. The brace has adjustable straps to secure the brace to the patient's arm. A retainer is coupled to the brace on the medial side of the arm. The retainer is configured to retain a flexible dynamic stiffener such that the stiffener extends from the medial side of the upper arm to the medial side of the forearm for impeding movement of the elbow joint.

Another embodiment of orthosis is designed to impede movement of a knee joint caused by muscle contraction. Like the elbow orthosis described above, the knee orthosis has a tubular brace with adjustable straps that secure the brace to a patient's leg. A retainer is coupled to the brace on the posterior side of the patient's leg and is configured to retain a flexible dynamic stiffener. The stiffener extends from the posterior side of the upper leg to the posterior side of the lower leg for impeding movement of the knee joint.

In a preferred embodiment, the flexible dynamic stiffener for any of the embodiments described above comprises a heat treated and tempered spring steel. In one aspect, the spring steel is Unified Numbering System G10950 steel. Preferably, the stiffener comprises steel having a yield tensile strength of between approximately 100 to 320 kilopounds per square inch, more preferably between approximately 150 to 275 kilopounds per square inch, even more preferably between approximately 200 to 250 kilopounds per square inch, and most preferably approximately 240 kilopounds per square inch. In one aspect, the stiffener comprises steel having a modulus of elasticity of between approximately 150 to 300 GPa, more preferably between approximately 175 to 250 GPa, and most preferably between approximately 190 to 210 GPa. Preferably, the stiffener comprises steel having a hardness on the Rockwell C scale of between approximately 45 to 60, more preferably between approximately 45 to 55, and most preferably between approximately 48 to 51.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
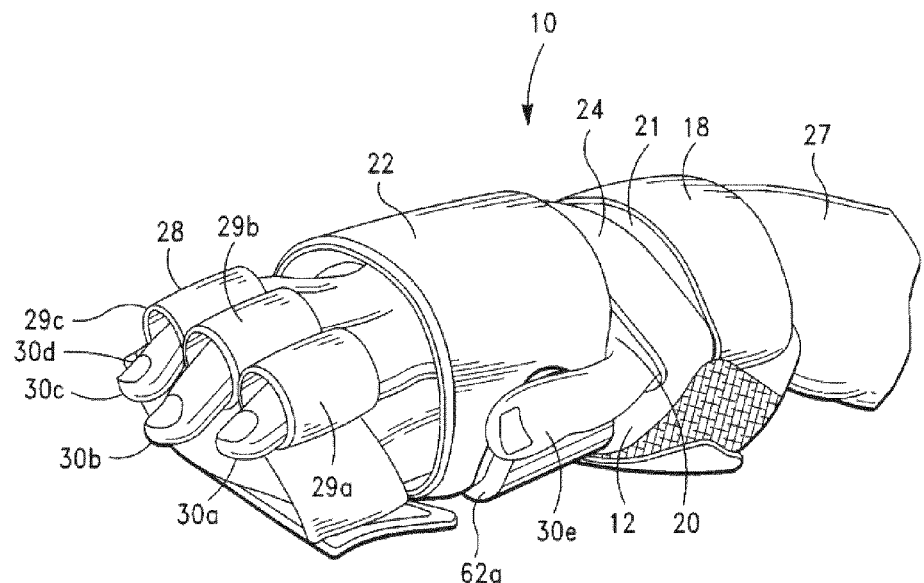
FIG. 1 is a front perspective view of a hand orthosis according to one embodiment of the present invention.

The present application is directed toward an orthosis having a flexible dynamic stiffener that is configured to extend across a joint and is elastic such that it rebounds to its original form after flexing due to joint movement caused by muscle contraction. While the orthosis could be designed to be used in conjunction with any articulating joint, four different types of orthoses are shown and described herein for illustration. Thus, while the present application only shows and describes hand/wrist, foot/ankle/toes, elbow, and knee orthoses, the application covers any type of orthosis having a flexible dynamic stiffener as described herein including hip/knee and hip/thigh orthoses.

First Embodiment

Hand/Wrist Orthosis

FIGS. 1-7 illustrate an orthosis for the hand and wrist in accordance with a first embodiment of the present invention. The hand and wrist orthosis 10 has a cover 12 (FIG. 1), a flexible stiffener 14 (FIGS. 5 & 6), which is positioned inside the cover, and opposed sheets 16a and 16b (FIG. 4), which encase the stiffener 14 for comfort. Cover 12 and opposed sheets 16a and 16b each have a shape that corresponds with the shape of stiffener 14. As shown in FIGS. 1-3C, a wrist strap 18 and one or more hand straps 22 and 24 are joined to cover 12 for securing a hand 20 and wrist 21 to the cover and stiffener. Further, a finger retainer 28 is joined to the cover and has a plurality of loops 29a, 29b, and 29c that respectively receive fingers 30a, 30b, and 30c in order to secure them to the cover. The loops 29a, 29h, and 29c are preferably spaced so that the fingers may alternatively reside between adjacent loops. Hand 20 also has a pinkie finger 30d resting on the top of cover 12 adjacent finger loop 29c.

Figure 3A:
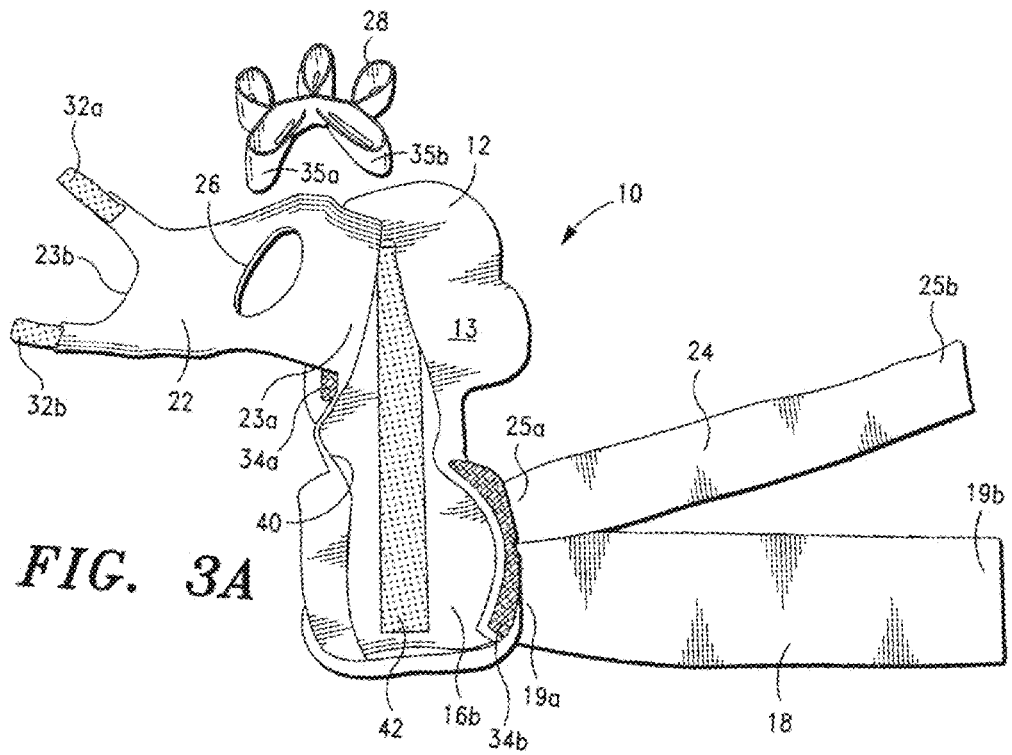
FIG. 3A is a bottom plan view of the orthosis of FIG. 1 showing it in a partially disassembled state.
Figure 3B:
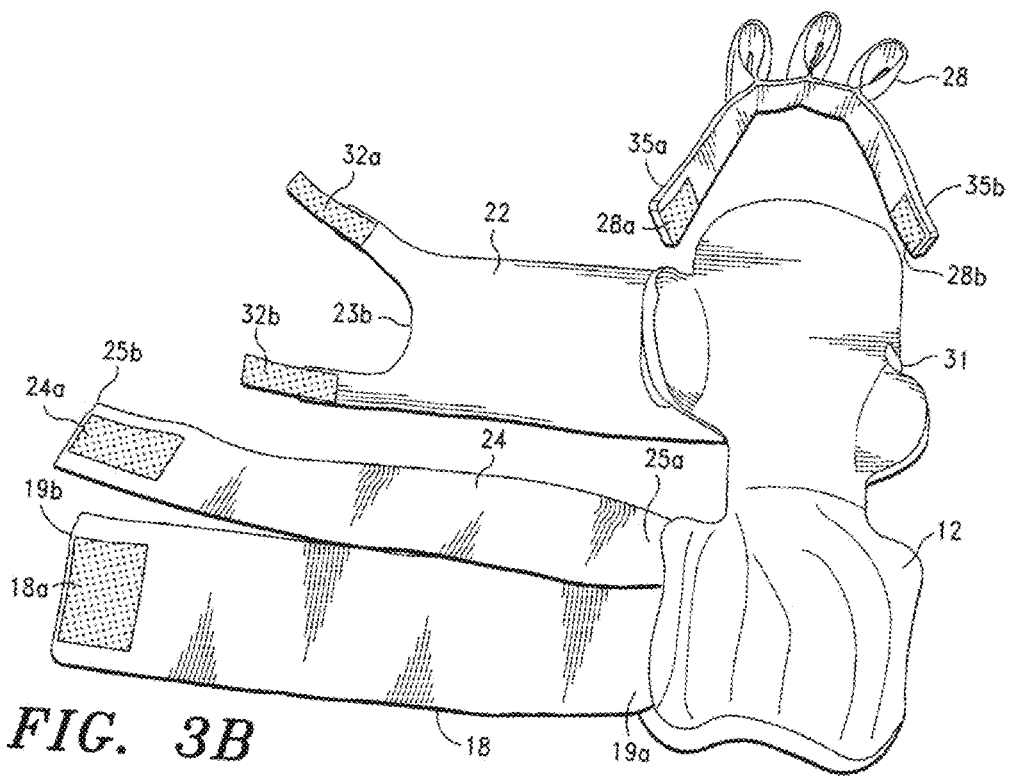
FIG. 3B is a top plan view of the orthosis of FIG. 1 showing it in a partially disassembled state.
Figure 3C:
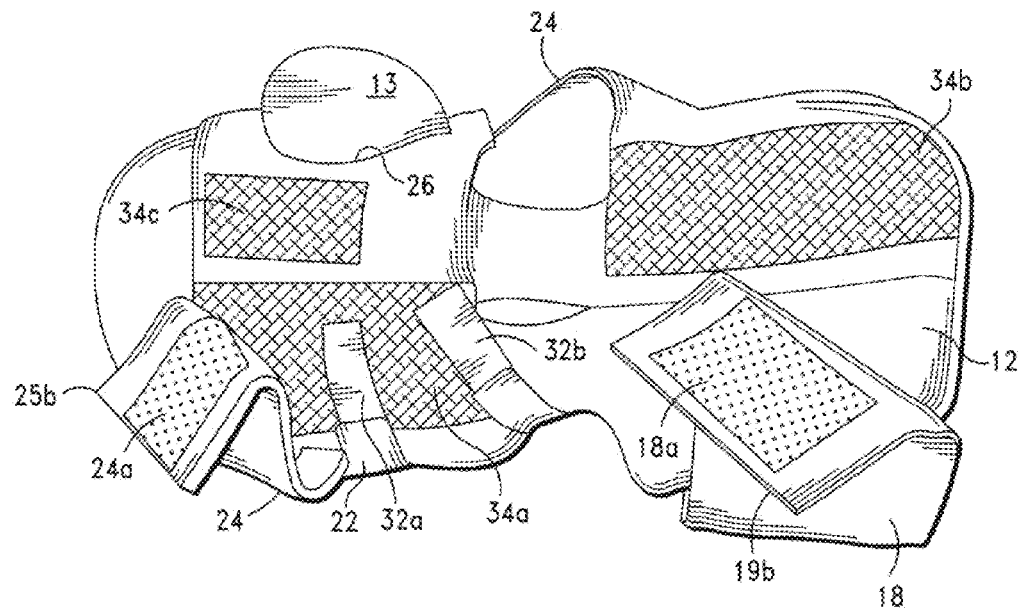
FIG. 3C is a bottom plan view of the orthosis of FIG. 1 showing where hand straps are removably secured to a cover of the orthosis.
Figure 5:
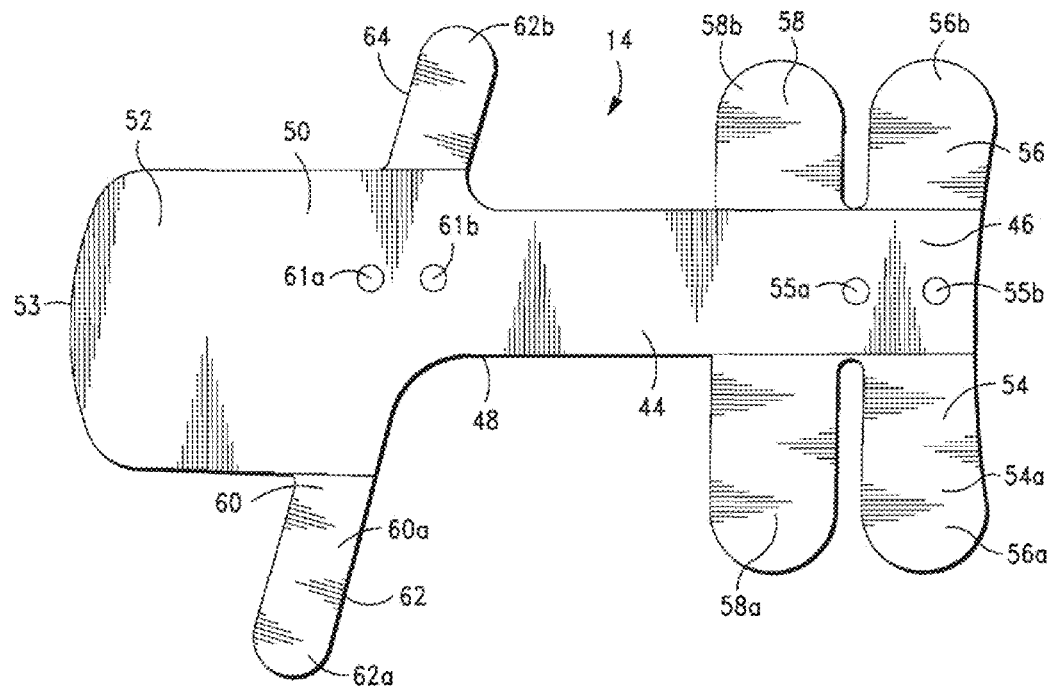
FIG. 5 is a top plan view of the stiffener of the orthosis of FIG. 1.

Referring now to FIGS. 3A & 3B, wrist strap 18 has a first end 19a stitched to the cover 12 and a second end 19b that has hook material 18a (FIG. 3B) of a hook and loop fastener stitched to it. Hand strap 22 has a first end 23a stitched to cover 12 and a second end 23b. Two spaced apart pieces of hook material 32a and 32b are stitched to second end 23b of hand strap 22. Hand strap 22 has an opening 26 for receiving an area 13 of cover 12. Area 13 of cover 12 resides over hand stabilizer section 62a of stiffener 14, which is shown in FIG. 5 and described in more detail below, when the orthosis is in use as shown in FIG. 1. Likewise, second end 23b of the hand strap 22 is C-shaped for receiving the hand stabilizer section 62b of stiffener 14, shown in FIG. 5, when the orthosis is in use. Hand strap 24 has a first end 25a stitched to cover 12 and a second end 25b that has hook material 24a (FIG. 3B) stitched to it.

As shown in FIGS. 2, 3A, 3B, and 3C, when the orthosis is in use the hook material 18a, 32a-b, and 24a joined to straps 18, 22, and 24, respectively, engages the bottom of cover 12 or loop material 34a, 34b, and 34c that is joined to the cover. The hook material 18a on strap 18 is preferably fastened to loop material 34b, while the hook material 32a and 32b on strap 22 is preferably fastened to loop material 34a. The hook material 24a on strap 24 preferably has a different color than the hook material 18a and 32a-b on straps 18 and 22. The color of hook material 24a is preferably the same as the color of loop material 34c to indicate that the hook material 24a is supposed to be fastened to loop material 34c. Additionally, there is a loop of fabric 31 (FIG. 3B) sewn to the top side of cover 12 that is the same color as hook material 24a and loop material 34c. This loop 31 indicates that strap 24 is positioned over the loop 31 before hook material 24a is secured to loop material 34c. Preferably, hook material 24a, loop material 34c, and loop of fabric 31 are red, while hook material 18a and 32a-b, and loop material 34a and 34b are black to assist the user in properly fastening the device.

Preferably, cover 12 is formed from a material that can engage the hook material 18a, 32a-b, and 24a joined to the second ends of straps 18, 22, and 24 in a similar manner as loop material. Cover 12 is preferably made from a soft material such as cotton, polyester, or a blend thereof, although cover 12 may be made from any suitable material. Using hook and loop material to fasten the straps to the cover enables the straps to be adjustable so that different sized hands and wrists may be secured to the cover and stiffener. Finger retainer 28 also has opposite ends 35a and 35b, shown in FIGS. 2, 3A, and 3B that have hook material 28a, 28b (FIG. 3B) joined to them for removably and adjustably securing the finger retainer 28 to the cover 12.

Although the straps are shown as being removably and adjustably secured to the cover with hook and loop material, it is within the scope of the invention for the straps to be secured to the cover by any means known in the art, for example they may be secured with buttons, snaps, or ties. Further, each end of each strap may be permanently secured to the cover, for example using adhesive or stitching. In this embodiment the straps may be elastic so that they may expand and contract to secure hands and wrists of varying sizes to the cover and stiffener. Further, it will be appreciated that any number of straps of any shape and size may also be used to secure the hand and wrist to the cover. It is also within the scope of the invention for the straps to not be adjustable or to use a device other then straps to secure a hand and wrist to the cover and stiffener. Additionally, it is within the scope of the invention to use the orthosis without finger retainer 28. Further, the first ends 19a, 23a, and 25a of straps 18, 22, and 24 may be joined to the cover in a manner other than stitching, such as adhesive. The straps may also be integral with the cover instead of being stitched to the cover. It is also within the scope of the invention for the hook and loop material to be joined to the straps and cover in a manner other than stitching, such as adhesive.

Figure 2:
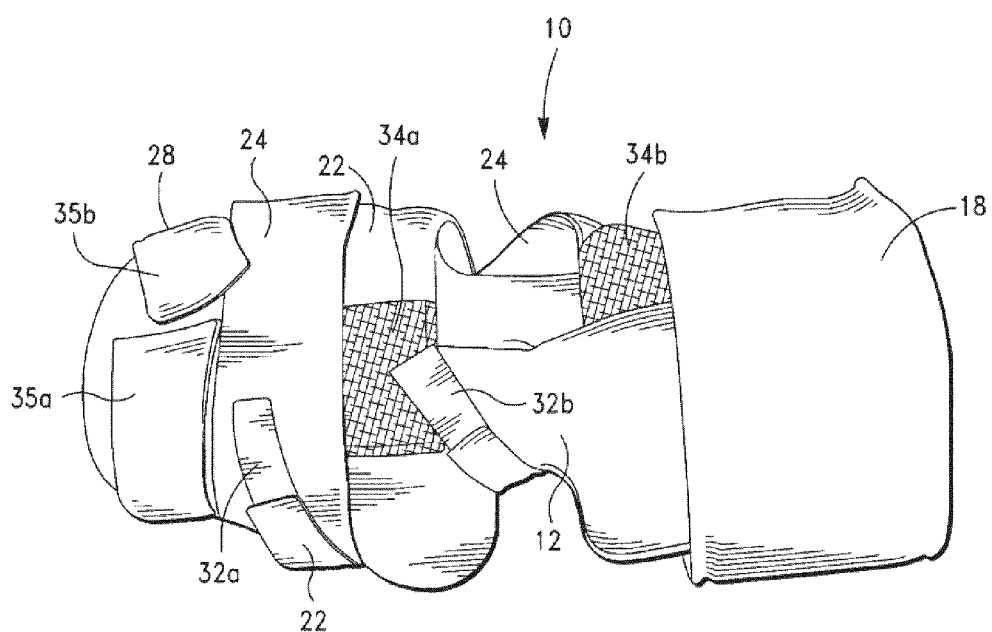
FIG. 2 is a bottom plan view of the orthosis of FIG. 1.

As shown in FIG. 3A, there is an opening 40 in the back of cover 12 for receiving stiffener 14 and the sheets 16a and 16b that encase the stiffener. Opening 40 facilitates removal of the stiffener 14 and sheets 16a and 16b from the cover 12 for cleaning the cover or replacing the stiffener. A strip of hook material 42 is adhered to the back of sheet 16b. Thus, when the opening 40 is closed to form the orthosis, as shown in FIG. 2, the hook material 42 engages the inner surfaces of cover 12 that are adjacent to the opening 40.

Figure 4:
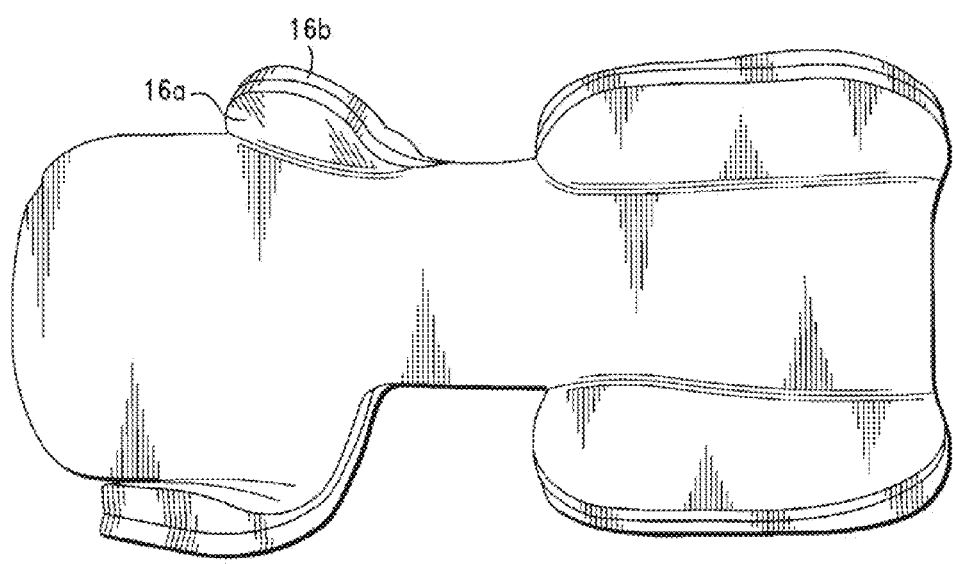
FIG. 4 is a top plan view of an encased stiffener of the orthosis of FIG. 1.

Referring now to FIG. 4, the inner surfaces of sheets 16a and 16b are joined along their peripheral edges with adhesive in order to encase stiffener 14. It is within the scope of the invention however for the sheets to be joined by any other means known in the art including hook and loop fasteners or thermal bonding. The sheets are preferably a soft resilient foam or fabric for comfort; however, the sheets may be made from any suitable material. It is also within the scope of the invention for the orthosis to not have sheets 16a and 16b encasing the stiffener 14 or for the sheets 16a and 16b to be integrally formed such that a single sheet encases the stiffener 14.

Figure 6:
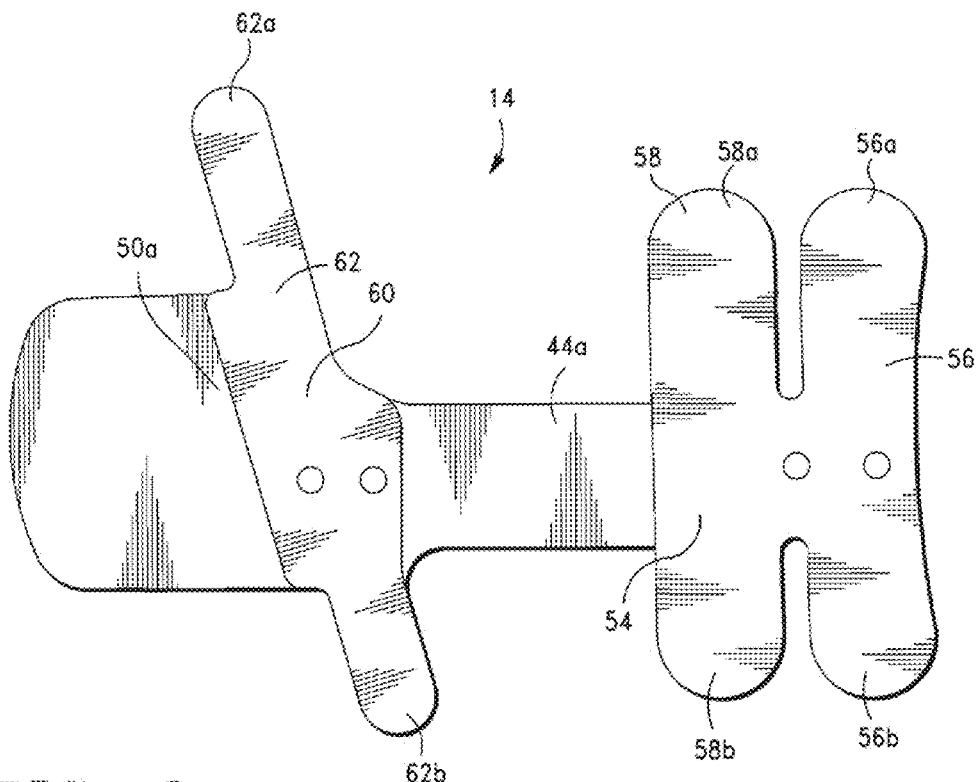
FIG. 6 is a bottom plan view of the stiffener of FIG. 5.

As shown in FIGS. 5 and 6, stiffener 14 has an elongate midportion 44 with a forearm end 46 that is positioned adjacent to a forearm when the orthosis is worn and an opposite wrist end 48 that is positioned adjacent to a wrist. A palm portion 50 extends distally from the wrist end of the midportion, a finger portion 52 extends distally from the palm portion 50, and the finger portion 52 terminates at a distal end 53. Preferably, the integral midportion 44, palm portion 50, and finger portion 52 are generally planar when they are not flexed due to wrist and finger movement.

The stiffener 14 also preferably comprises one or more wrist and/or forearm stabilizers. As shown in FIGS. 5 and 6, a first sheet 54 is joined to the forearm end 46 of the midportion with rivets 55a and 55b such that the top surface 54a of first sheet 54 is in contact with the bottom surface 44a of midportion 44. While the first sheet 54 is joined to the forearm end 46 with rivets, it is within the scope of the invention for the first sheet and forearm end to be joined by any method. For example, the first sheet 54 and forearm end 46 may be joined by welding, with screws, or with other fasteners. Sheet 54 has forearm stabilizers 56 and 58 that each extend from opposite sides (laterally and medially) of the forearm end 46 of the midportion 44. Forearm stabilizers 56 and 58 have substantially the same form. Forearm stabilizer 56 has two forearm stabilizer portions 56a and 56b extending outward medially and laterally from midportion 44. Forearm stabilizer 58 likewise has two forearm stabilizer portions 58a and 58b extending outward medially and laterally from midportion 44. The lateral and medial sections of the forearm stabilizers 56 and 58 are bent upward with respect to midportion 44 to form a generally C-shaped channel for retaining a forearm 27 as shown by the configuration in FIG. 1. There is preferably a gap between portions 56a and 58a (and portions 56b and 58b) in order to facilitate bending the forearm stabilizers upward and shaping the stabilizers to retain a forearm. The outer peripheral edges of each of portions 56a, 56b, 58a, and 58b are preferably rounded for safety and comfort.

A second sheet 60 is joined to the palm portion 50 with rivets 61a and 61b such that the top surface 60a of second sheet 60 is in contact with the bottom surface 50a of palm portion 50. While the second sheet 60 is joined to the palm portion 50 with rivets, it is within the scope of the invention for the second sheet and palm portion to be joined by any method. For example, the second sheet 60 and palm portion 50 may be joined by welding, with screws, or with other fasteners. Second sheet 60 has a hand stabilizer 62 comprised of two hand stabilizer sections 62a and 62b that extend from opposite sides (laterally and medially) of the palm portion. As shown in FIG. 1, the hand stabilizer 62 can be bent upward with respect to palm portion 50 for retaining hand 20. Thumb 30e wraps around hand stabilizer section 62a and rests on its outer surface. Although thumb 30e is shown in this position, the thumb may be positioned in any manner including inside of the stabilizer section 62a adjacent to the index finger 30a or with its tip on the bottom surface of cover 12. The outer peripheral edges of each of hand stabilizer sections 62a and 62b are preferably rounded for safety and comfort.

Midportion 44, palm portion 50, and finger portion 52 are integrally formed from a dynamic flexible material that resists flexing to impede flexion of wrist 21 and fingers 30a-d, shown in FIG. 1, but allows some movement in the finger joints and wrist joint. The material is also elastic so that the stiffener rebounds to its original form after flexing due to movement of the wrist and fingers caused by muscle contraction.

In a preferred aspect, first and second sheets 54 and 60 are formed from a second material that plastically deforms when the forearm stabilizers 56 and 58 and hand stabilizer 62 are bent upward as generally shown in FIG. 1 to retain the forearm 27 and hand 20 respectively. Once in the proper configuration for a particular user, the forearm stabilizers 56, 58 and hand stabilizer 62 do not bend under normal use by the patient. Although first and second sheets 54 and 60 are preferably made from a material that plastically deforms to a fixed static position during use, these sheets may also be made from the same flexible dynamic material used for the midportion 44, palm portion 50, and finger portion 52. In this alternative embodiment, the first and second sheets 54 and 60 may be integral with the midportion 44, palm portion 50, and finger portion 52. Additionally, it is within the scope of the invention for the orthosis to not have first and second sheets 54 and 60 and omit one or more of forearm stabilizers 56 and 58 or hand stabilizer 62.

The midportion 44, palm portion 50, and finger portion 52 are preferably constructed from a heat treated and tempered spring steel. However, it is within the scope of the invention for the midportion 44, palm portion 50, and finger portion 52 to be made from any dynamic flexible material that resists flexing but rebounds to its original form after flexing due to movement of the wrist and fingers. Preferably, the midportion 44, palm portion 50, and finger portion 52 are made from a spring steel having a Unified Numbering System identifier of G10950, or a designation of 1095 steel from the American Iron and Steel Institute ("AISI"). Preferably, the steel comprises between approximately 0.9 to 1.05% carbon, 0.3 to 0.5% manganese, 0.15 to 0.30% silicon, and no more than 0.040% phosphorus and 0.050% sulfur. Preferably, the steel has a modulus of elasticity of between approximately 150 to 300 GPa, more preferably between approximately 175 to 250 GPa, and most preferably between approximately 190 to 210 GPa. Preferably, the steel is heat treated and tempered so that it has a yield tensile strength of between approximately 100 to 320 kilopounds per square inch, more preferably between approximately 150 to 275 kilopounds per square inch, even more preferably between approximately 200 to 250 kilopounds per square inch, and most preferably approximately 240 kilopounds per square inch. Preferably, the steel has a hardness on the Rockwell C scale of between approximately 45 to 60, more preferably between approximately 45 to 55, and most preferably between approximately 48 to 51.

Preferably, first and second sheets 54 and 60 are made from cold rolled steel having a relatively low carbon composition. One type of steel suitable for first and second sheets 54 and 60 is steel having a Unified Numbering System identifier of G10180, or steel designated as 1018 by the AISI, which is a steel comprising between approximately 0.14 to 0.20% carbon. Preferably, the material used for the first and second sheets 54 and 60 has a yield tensile strength and a hardness that is less than the yield tensile strength and hardness of midportion 44, palm portion 50, and finger portion 52 such that the first and second sheets 54 and 60 are readily deformable without special tools. Preferably, the first and second sheets 54 and 60 are made from a material with a yield tensile strength that is between approximately 20 to 100 kilopounds per square inch, and the hardness of the sheets is between approximately 50-100 on the Rockwell B scale or between 20-40 on the Rockwell C scale. Preferably, the first and second sheets 54 and 60 are made from a material with a modulus of elasticity of between approximately 29,000 to 31,000 kilopounds per square inch. Although the first and second sheets 54 and 60 are preferably made from steel having the above listed properties, it is within the scope of the invention for the first and second sheets to be made from any material. For example, the first and second sheets may be made from steel designated as 1006, 1010, 1015, 1020, 1030, or 1035 by the AISI. Further, the first and second sheets may be made from any other type of metal or polymeric material.

Figure 7:
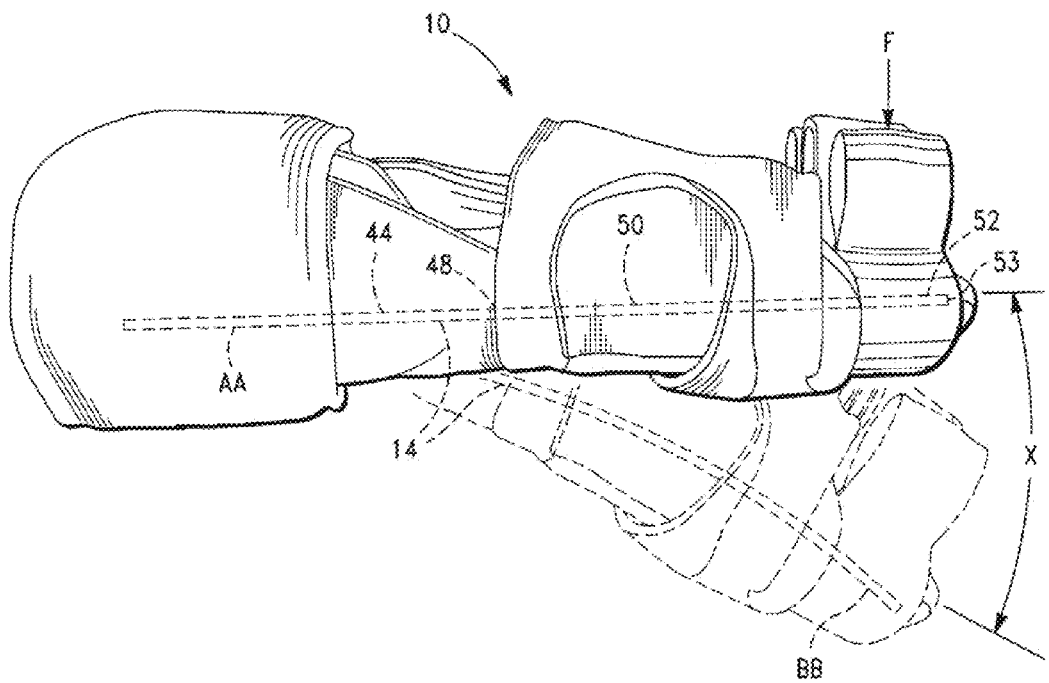
FIG. 7 is a side elevational view of the orthosis of FIG. 1 showing the orthosis in a flexed position in dashed lines.

FIG. 7 illustrates operation of the hand/wrist orthosis. For illustration, the stiffener 14 (shown in dashed lines) is positioned in a first configuration AA, which is substantially planar. When the patient's muscle contraction causes a force F to be applied to the distal end 53 of finger portion 52, the stiffener 14 is dynamically positioned in a second configuration BB, such that the distal end 53 of finger portion 52 of stiffener 14 exhibits an angular displacement of X degrees. When the force F subsides, the stiffener's dynamic elastic properties cause it to return to its first configuration AA. When the orthosis and stiffener are in use, it should be appreciated to those skilled in the art that flexion of the wrist and/or fingers will exert a pressure across the various parts of the stiffener and not a force that is located at a single location. However, a resultant force at a particular location can be calculated based on the pressure distribution across the stiffener. The force F shown in FIG. 7 represents a resultant force that can be calculated based on a typical pressure or force distribution across the stiffener caused by wrist and/or finger flexion. Preferably, the midportion 44, palm portion 50, and finger portion 52 of stiffener 14 are sized and made from a material with physical properties such that the angle X is between approximately 20 to 60 degrees when force F is approximately 20 pounds. It should be understood, however, that the material properties and dimensions of the stiffener may be altered so that the stiffener has any desired range of movement for a typical force exerted on it by any given patient.

When the stiffener is subjected to wrist or finger flexion as shown in FIG. 7 it typically flexes at approximately the wrist end 48 of midportion 44. It should be appreciated that the thickness and width of the stiffener at the location where the stiffener flexes, the distance between where the stiffener flexes to where the resultant force F is located, and the properties of the stiffener material, specifically its modulus of elasticity, each have an effect on the amount of angular displacement X that results from a given force F. Increasing the thickness, width, or distance between where the stiffener flexes from the distal end 53 will decrease the angular displacement X for any given force F. Preferably, the stiffener 14 has a thickness of between approximately 0.002 to 0.07 inches, more preferably a thickness of between approximately 0.005 to 0.04 inches, and most preferably a thickness of between approximately 0.008 to 0.025 inches. While the distance between where the stiffener flexes to where the resultant force F is located can vary based on the size of the user's hand and fingers, preferably this distance is between approximately 3 to 9 inches. Preferably, the width of midportion 44 is between approximately 1 to 3 inches and most preferably is approximately 1.375 inches. Preferably, the width of the palm portion 50 is between approximately 2 to 5 inches and most preferably is approximately 3 inches. Preferably, the width of the finger portion 52 is between approximately 2 to 4 inches and most preferably is approximately 3 inches. It should also be understood that each of the midportion 44, palm portion 50, and finger portion 52 may have a variable width or thickness.

Figure 8:
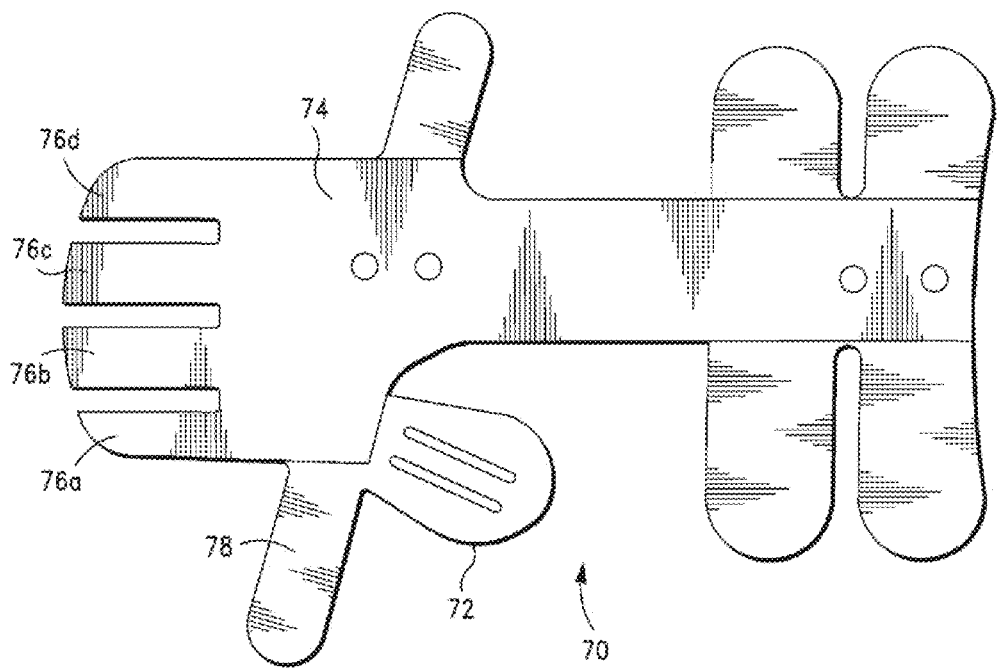
FIG. 8 is a top plan view of an alternative embodiment of stiffener for use with a hand orthosis similar to the orthosis of FIG. 1.

FIG. 8 shows an alternate embodiment of stiffener 70 that may be used with a modified version of orthosis 10 that has a cover having a shape and size which will accommodate stiffener 70. Stiffener 70 is substantially similar to stiffener 14 except that stiffener 70 has a plurality of elongate finger sections 76a, 76b, 76c, and 76d that each extend distally from palm portion 74. Finger sections 76a-d flex independently of each other to allow individual movement of fingers that are secured to a hand orthosis having stiffener 70. Thus, each finger section 76a-d provides a dynamic resistance during use. The finger sections are integral with palm portion 74 and preferably constructed from one of the materials specified above with respect to midportion 44, palm portion 50, and finger portion 52 of stiffener 14.

The stiffener 70 also has a thumb abductor 72 that is integral with hand stabilizer 78. The thumb abductor 72 is preferably plastically deformable such that it may be bent downward with respect to the palm portion for supporting a thumb. Preferably, thumb abductor 72 is made from one of the materials specified above with respect to first and second sheets 54 and 60 of stiffener 14, shown in FIGS. 5 and 6. The thumb abductor 72 is plastically deformed into the desired position to conform to the shape of the thumb joint. However, the thumb abductor is made from a material such that it will resist forces to which it is normally subjected when worn by a patient. That is, during contracture, the patient is unable to move the thumb abductor 72 of the stiffener 70 during use such that the stiffener provides a static resistance to the joint.

Second Embodiment

Foot Orthosis

Figure 9:
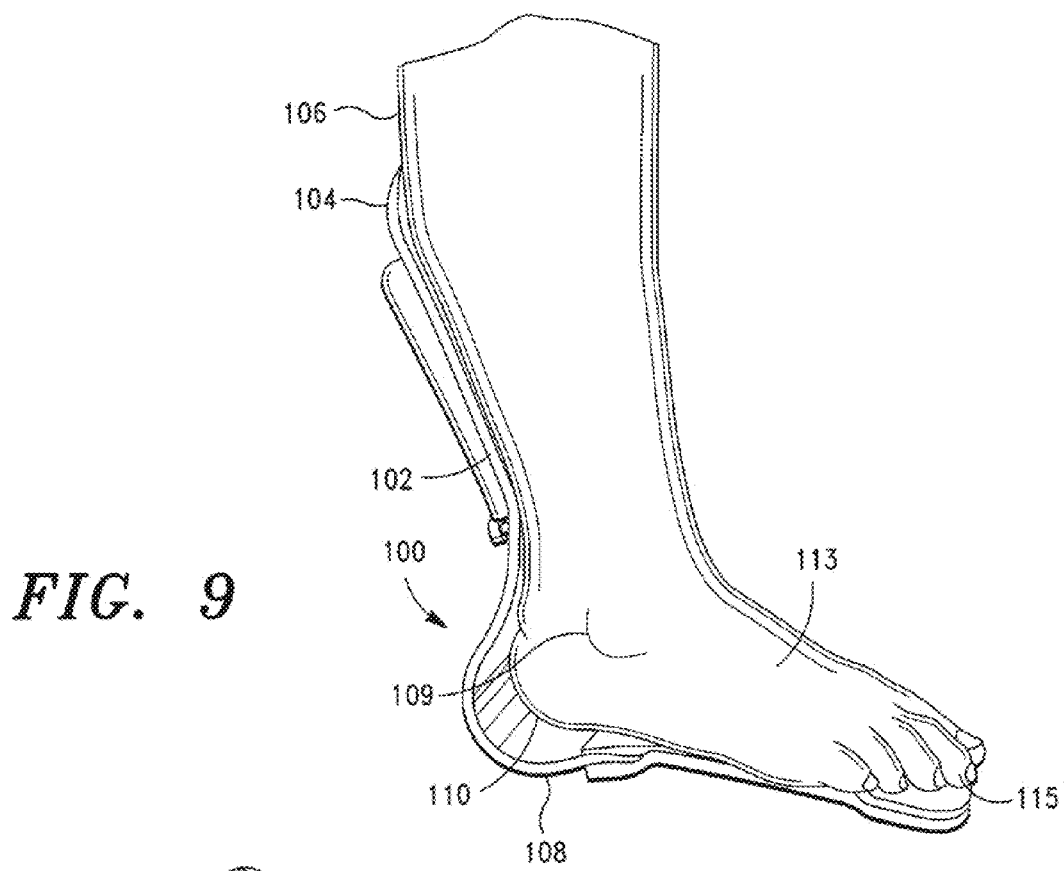
FIG. 9 is a perspective view of a foot orthosis according to another embodiment of the present invention.
Figure 10:
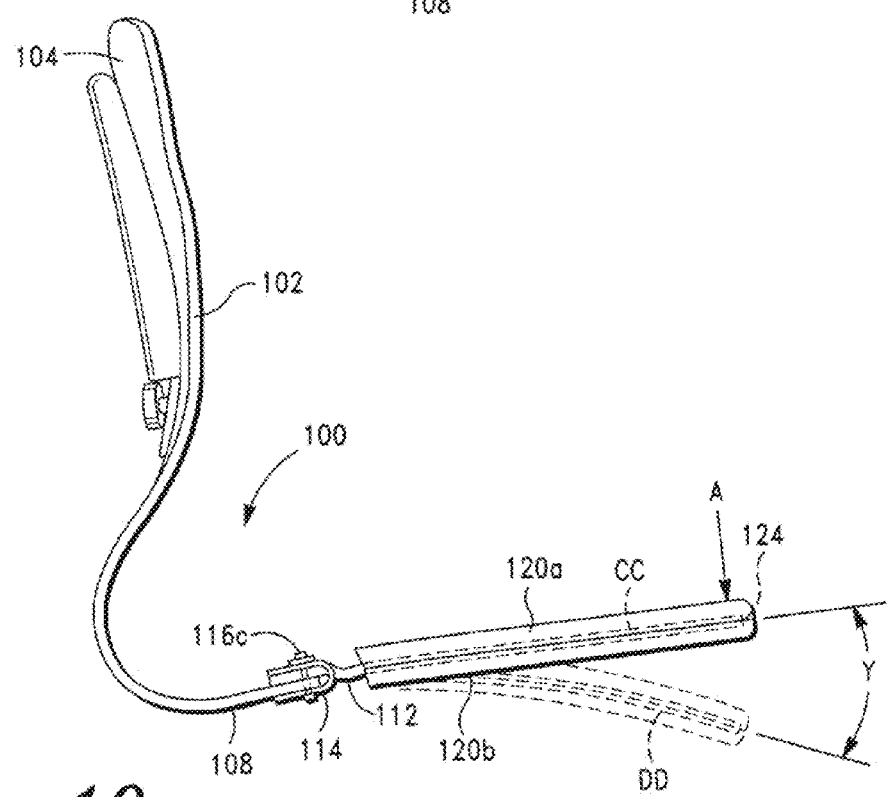
FIG. 10 is a side elevational view of the orthosis of FIG. 9 showing the orthosis in a flexed position in dashed lines.
Figure 11:
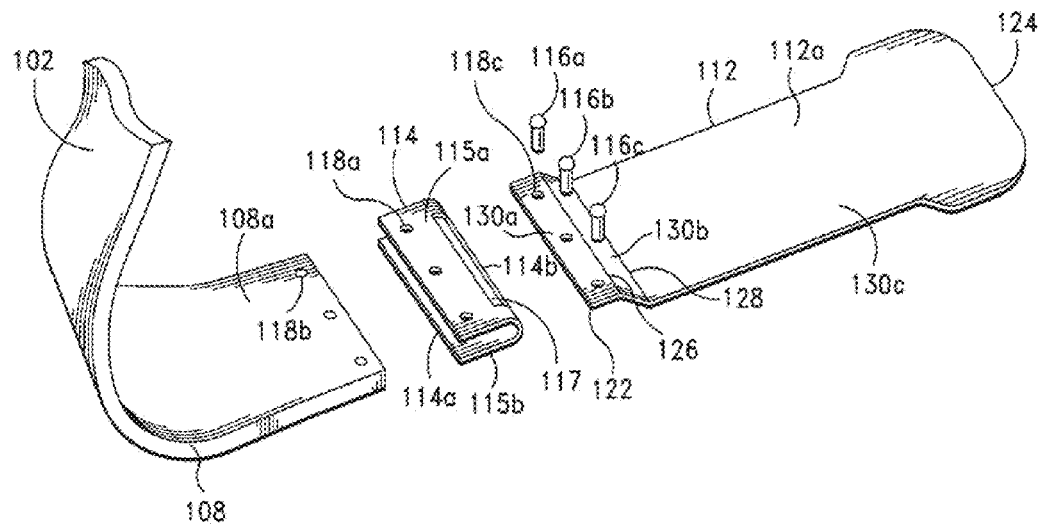
FIG. 11 is a partial perspective view of the orthosis of FIG. 9 in a disassembled state.

Referring now to FIGS. 9-11, a foot orthosis in accordance with a second embodiment of the present invention is shown as 100. The foot orthosis has an L-shaped splint 102 with a first end 104 positioned adjacent to a posterior lower leg 106 and an opposite heel end 108 positioned underneath a heel 110. A flexible stiffener 112, shown in FIGS. 10 and 11, is joined to the heel end 108 of the splint. Preferably the stiffener is joined using a retaining clip 114 and one or more rivets 116a, 116b, and 116c. As shown in FIG. 9, the stiffener is positioned underneath foot 113 and toes, one of which is identified as 115, to impede downward movement of the foot and/or toes.

Referring to FIG. 11, retaining clip 114 is U-shaped with two legs 115a and 115b each having a free end 114a and a joined end 114b. The distance between the free ends 114a of the legs 115a and 115b is slightly greater than the combined thickness of the heel end 108 of the splint and the stiffener 112. When the clip and stiffener are assembled on splint 102, as shown in FIG. 10, the bottom surface of stiffener 112 is in contact with the top surface 108a of the heel end 108 of the splint, and the top surface 112a of stiffener 112 is in contact with an inside surface of leg 115a of clip 114. As shown in FIG. 11, there are one or more holes 118a, 118b, and 118c in retaining clip 114, splint 102, and stiffener 112, respectively, that align to receive rivet 116a. Likewise, there are holes in the retaining clip, splint, and stiffener that align to receive rivets 116b and 116c. There is an elongate opening 117 in retaining clip 114 that is sized to receive stiffener 112 for securing the stiffener to the splint. Although splint 102 and stiffener 112 are shown as being joined with retaining clip 114 and rivets 116a-c, it is within the scope of the invention for the splint and stiffener to be joined by any means, for example screws, adhesive, tacks, ties, buttons, snaps, and the like.

Referring to FIG. 10, stiffener 112 is preferably encased by one or more sheets 120a and 120b. The sheets 120a and 120b also preferably encase retaining clip 114 and a portion of the heel end 108 of splint 102 (although this is not shown in FIG. 10 in order to show how the stiffener 112 joins to the splint 102). Sheets 120a and 120b are preferably a soft resilient foam joined with adhesive. However, the sheets may be made from any suitable material and joined together using any suitable means as discussed above. It is also within the scope of the invention for the foot orthosis 100 to not have sheets 120a and 120b encasing the stiffener 112.

Preferably, splint 102 and stiffener 112 are secured to lower leg 106 and foot 113 via a fabric boot such as the one shown and described in U.S. Pat. No. 7,163,519 to Price et al., which is hereby incorporated by reference in its entirety. The fabric boot may be secured to splint 102 and stiffener 112 via hook and loop fasteners or by any other fastening method. Preferably, the fabric boot has at least one leg strap that is joined to the boot and that is configured to secure the boot to lower leg 106 and at least one foot strap that is joined to the boot and that is configured to secure the boot to foot 113. However, other types of boots or covers for securely fastening splint 102 and stiffener 112 to a lower leg and foot are within the scope of the invention. Splint 102 is preferably constructed of a rigid transparent plastic such as polyvinylchloride; however it may be made from any suitable rigid material. While preferably splint 102 is transparent, it is within the scope of the invention for the splint to have any color. Stiffener 112 is preferably constructed from one of the materials specified above for stiffener 14.

As shown in FIG. 11, stiffener 112 has a first end 122 that is joined to the heel end 108 of the splint and a second end 124 that is positioned adjacent to toes 115 for impeding downward movement or flexion of the ankle 109 (FIG. 9) and/or toes 115. Between the ends 122 and 124, there are two bends 126, 128 in the stiffener 112 that are each approximately 45 degrees. The two bends form three surfaces 130a, 130b, and 130c in the stiffener 112 with surfaces 130a and 130c being substantially parallel. The bends 126 and 128 preferably position surface 130c and end 124 in a desirable position to support foot 113 and toes 115.

Stiffener 112 is elastic such that it rebounds to its original form after flexion of the ankle and/or toes caused by muscle contraction. The stiffener is made of a dynamic flexible material that resists flexing to impede flexion of the ankle and/or toes, but allows some movement in the joints. For illustration, the stiffener 112 (shown in dashed lines in FIG. 10) is positioned in a first configuration CC, which is substantially planar. When the patient's muscle contraction causes a force A to be applied to the second end 124, the stiffener 112 is dynamically positioned in a second configuration DD, such that the second end 124 of the stiffener 112 exhibits an angular displacement of Y degrees. When the force A subsides, the stiffener 112 returns to its first configuration CC. When the orthosis and stiffener are in use, it should be appreciated to those skilled in the art that flexion of the ankle and/or toes will exert a pressure across the various parts of the stiffener and not a force that is located at a single location. However, a resultant force at a particular location can be calculated based on the pressure distribution across the stiffener. The force A shown in FIG. 10 represents a resultant force that can be calculated based on a typical pressure or force distribution across the stiffener caused by ankle and/or toe flexion. Preferably, when force A is approximately 20 pounds the angle Y is between 0 to 65 degrees, more preferably between 0 to 45 degrees, and most preferably between 20 to 45 degrees. It should be understood, however, that the material properties and dimensions of the stiffener may be altered so that the stiffener has any desired range of movement for a typical force exerted on it by any given patient.

Ankle and/or toe flexion causes the stiffener 112 of the foot orthosis 100 to flex at approximately the location of bends 126 and 128. As discussed above with respect to the hand orthosis of the first embodiment, it should be appreciated that the amount of angular displacement Y for a given force A depends on the thickness of the stiffener at the location where it flexes, the width of the stiffener at the location where it flexes, the distance between where the stiffener flexes and the location of the resultant force A, and the properties of the material that the stiffener is made from. While the distance between where the stiffener flexes and the resultant force A can vary based on the size of the user's foot and toes, preferably this distance is between approximately 3 to 9 inches. Preferably, the width of the stiffener at the location of bends 126 and 128 is between approximately 2 to 3.5 inches and most preferably is approximately 2.625 inches. Preferably, the thickness of the stiffener is between approximately 0.002 to 0.07 inches, more preferably between approximately 0.005 to 0.04 inches, and most preferably between approximately 0.008 to 0.025 inches.

Third Embodiment

Elbow Orthosis

FIGS. 12-15 show an elbow orthosis 200 in accordance with a third embodiment of the present invention. The elbow orthosis has a tubular brace 202 that receives an arm 204 and extends across an elbow (not shown) from an upper arm 204a to a forearm 204b. As shown in FIGS. 13B and 13C, hook material 203a and 203b (FIG. 13B) is stitched to the inner surface of brace 202, and loop material 205a and 205b (FIG. 13C) is stitched to the outer surface of the brace. To secure the brace 202 to arm 204 the arm 204 is positioned over brace 202 so that the medial side of the elbow (not shown) is adjacent to the hole 202a shown in FIG. 13B. Then the brace 202 is wrapped around the arm 204 so that the hook material 203a and 203b engages the loop material 205a and 205b, respectively.

Figure 13A:
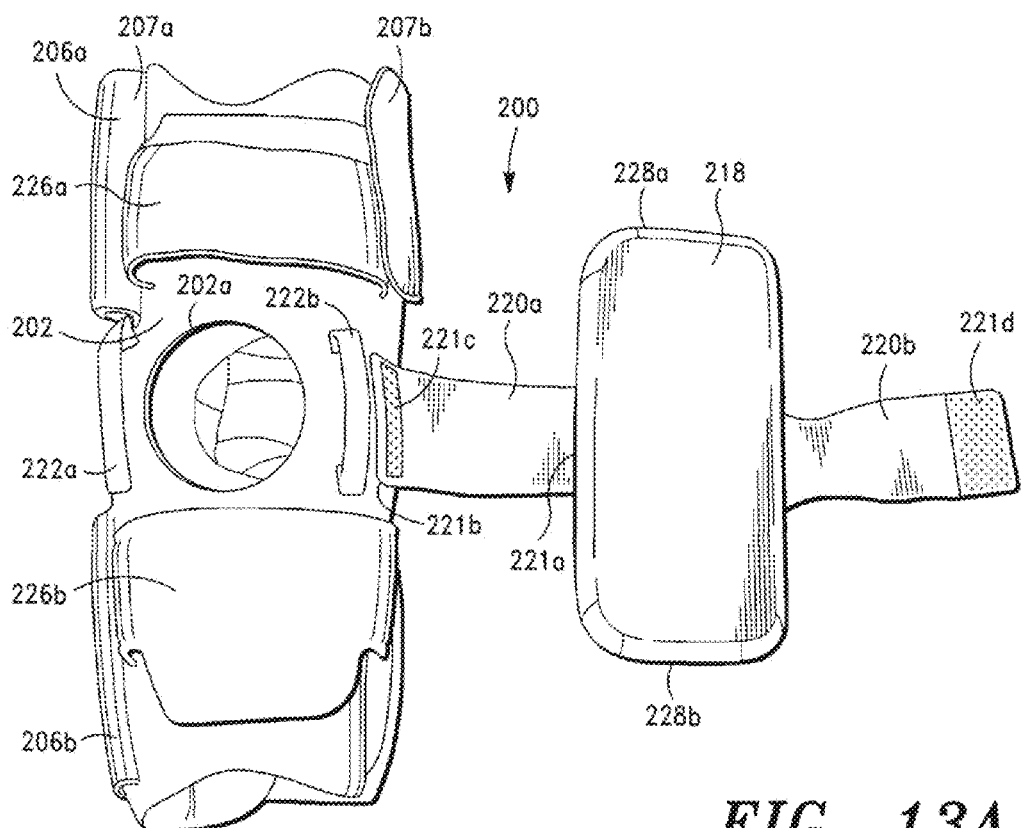
FIG. 13A is a bottom plan view of the orthosis of FIG. 12 showing a retainer in a disassembled state.
Figure 13B:
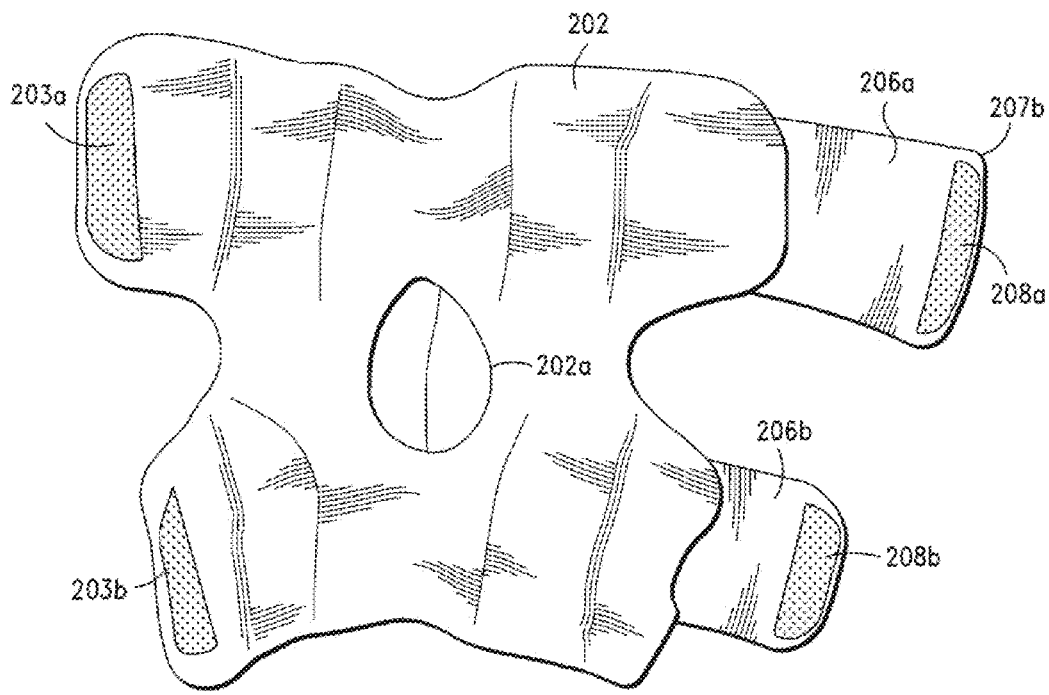
FIG. 13B is a top plan view of the orthosis of FIG. 12 showing it in a partially disassembled state.

The brace also has one or more adjustable upper and lower straps 206a and 206b to secure the brace to arm 204. As shown in FIG. 13A, upper strap 206a has one end 207a that is stitched to brace 202 and a second end 207b that has hook material 208a (FIG. 13B) joined to its inner surface for engagement with corresponding loop material 209a (FIG. 13C) on the brace 202. Alternatively, the hook material 208a on upper strap 206a may engage directly with the outer surface of brace 202 for securing the brace to arm 204. Lower strap 206b has hook material 208b (FIG. 13B) joined to its inner surface for engagement with loop material 209b (FIG. 13C) on brace 202 in a similar manner as upper strap 206a. Although the straps and brace are preferably adjustably joined with hook and loop material, it is within the scope of the invention for the straps and brace to be joined by any means. For example, each end of each strap may be permanently affixed to the brace 202 and the straps may be elastic so they can stretch to accommodate arms of different sizes.

Figure 12:
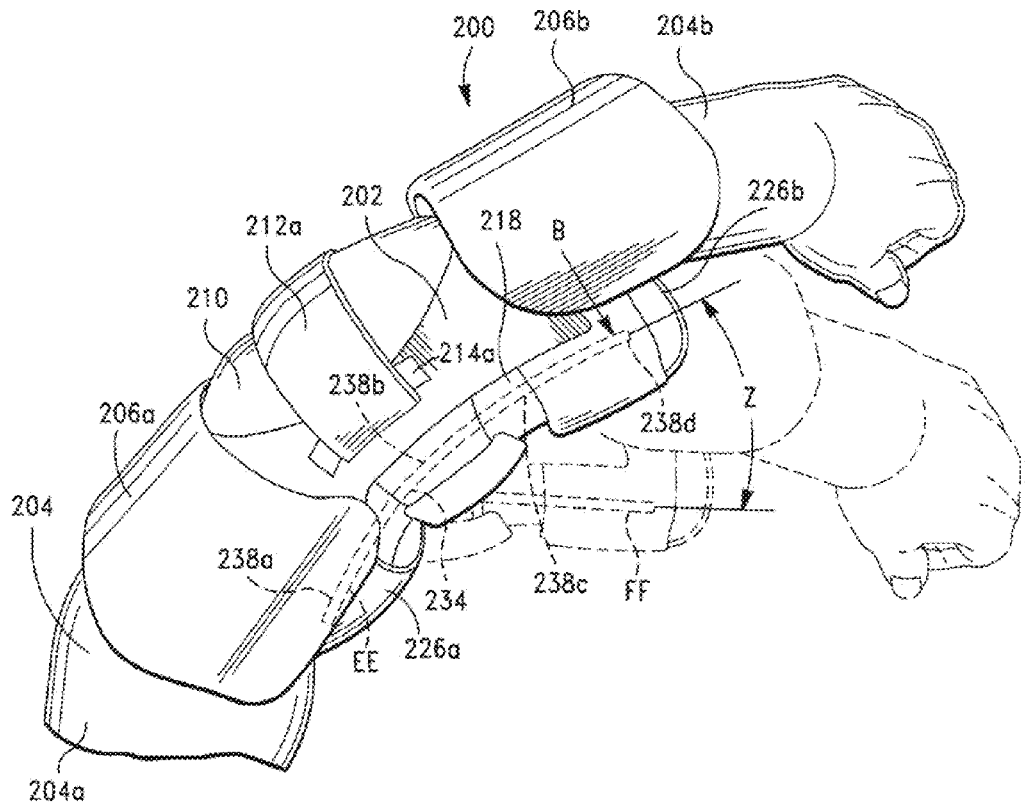
FIG. 12 is a perspective view of an elbow orthosis according to another embodiment of the present invention showing the orthosis in a flexed position in dashed lines.
Figure 13C:
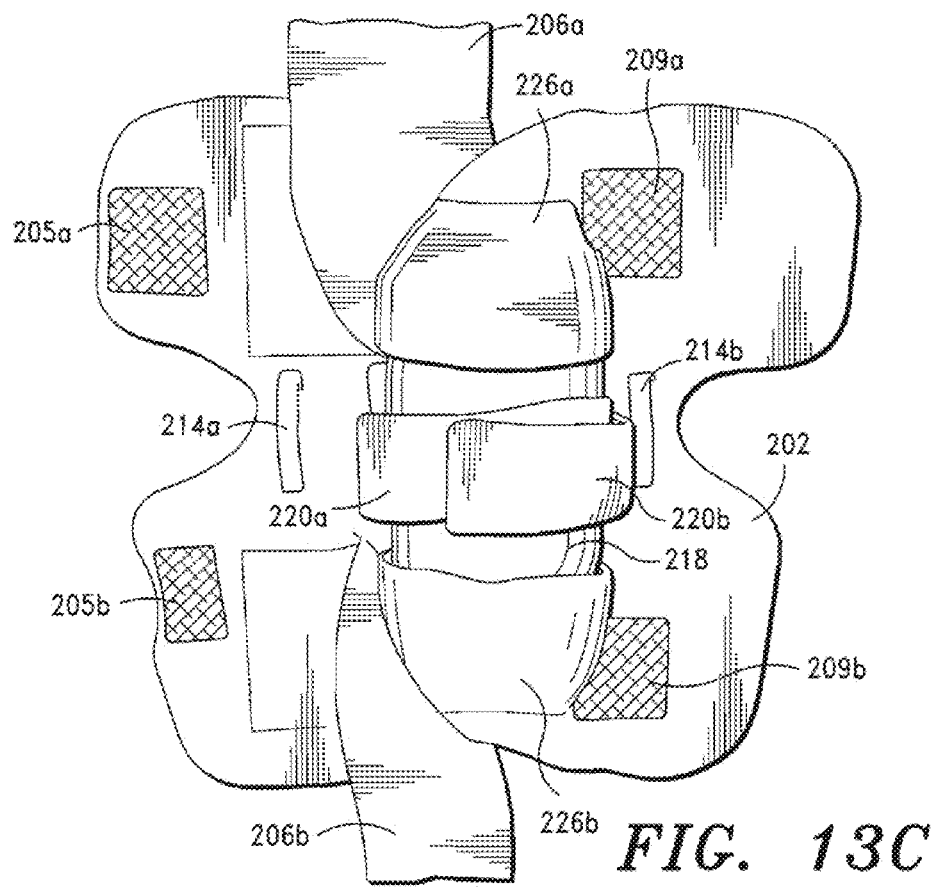
FIG. 13C is a bottom plan view of the orthosis of FIG. 12 showing it in a partially disassembled state.
Figure 13D:
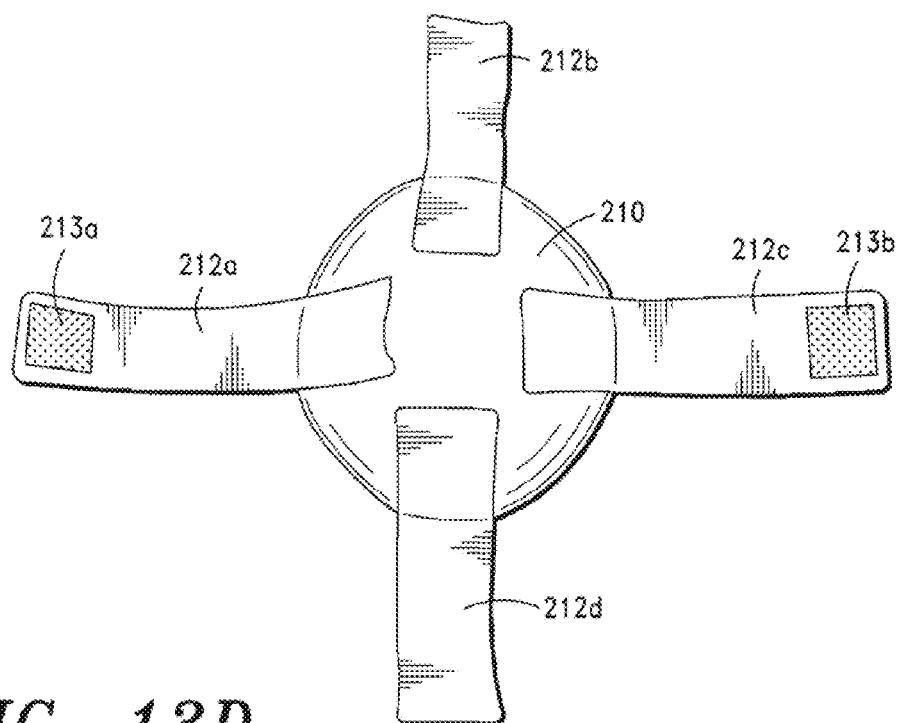
FIG. 13D is a top plan view of an elbow cap of the orthosis of FIG. 12.

FIGS. 12 and 13D show a circular, padded elbow cap 210 that is affixed to the brace 202. The elbow cap 210 has four equidistantly spaced straps 212a, 212b, 212c, and 212d extending from its outer peripheral edge. Strap 212a has a first end that is stitched to cap 210 and a second end with hook material 213a joined thereto. A portion of strap 212a between its first and second ends is received by a loop 214a, shown in FIGS. 12 and 13C, that is stitched to the outer surface of brace 202. As shown in FIG. 12, when the orthosis is assembled for use, the hook material 213a on strap 212a engages the outer surface of cap 210 near the center of the cap. Strap 212c also has a first end stitched to the cap 210 and a second end with hook material 213b joined thereto. Like strap 212a, a portion of strap 212c between its first and second ends is received by a loop 214b (FIG. 13C) that is stitched to the outer surface of brace 202. The hook material 213b on strap 212c engages the outer surface of cap 210 near the center of the cap in a similar manner as the hook material 213a on strap 212a. Straps 212b and 212d each have a first end stitched to cap 210 and a second end that has hook material, which is on the opposite side as that shown in FIG. 13D, joined to it for engagement with the outer surface of brace 202. When the cap 210 is secured to the brace 202 in the manner described above and shown in FIG. 12, the cap is positioned adjacent the lateral side of the elbow of arm 204. The cap 210 provides pressure against the elbow of arm 204 when the arm bends at the elbow. Using hook material to adjustably secure the straps 212a-d on elbow cap 210 to brace 202 allows the cap 210 and brace 202 to accommodate arms of different sizes. Although the cap is shown as being secured to the brace with straps having hook material, it is within the scope of the invention to secure the cap and brace by any other manner. It is also within the scope of the invention for the elbow orthosis 200 to not have a cap 210.

Figure 14:
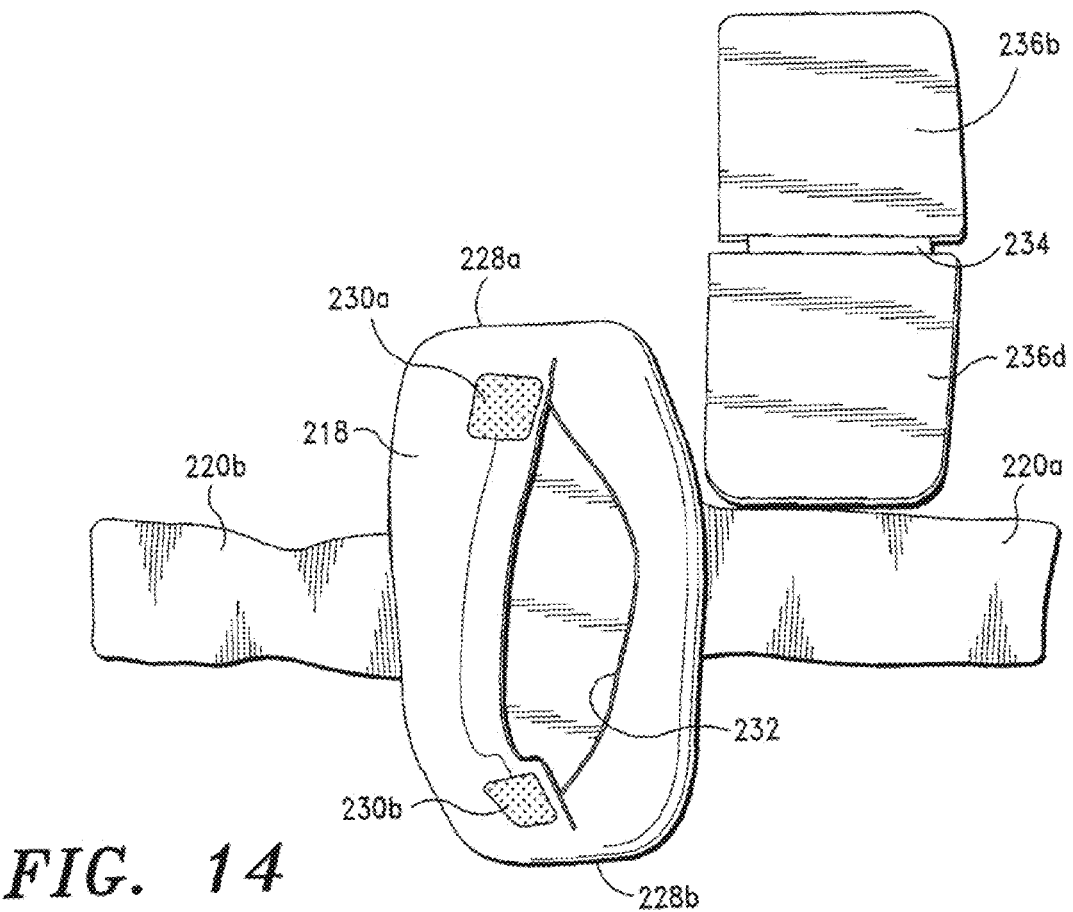
FIG. 14 is a top plan view of the retainer and encased stiffener of the orthosis of FIG. 12.

As shown in FIGS. 12 and 13C, a retainer 218 is releasably secured to brace 202 on the medial side of arm 204. As shown in FIGS. 13A, 13C, and 14, retainer 218 has two straps 220a and 220b extending outward from opposite sides of the retainer. Strap 220a has a first end 221a (FIG. 13A) that is stitched to retainer 218 and a second end 221b that has hook material 221c attached to it. A portion of strap 220a is received by a loop 222a (FIG. 13A) that is stitched to brace 202. When the retainer 218 is installed on brace 202, strap 220a passes through loop 222a and folds back over itself such that hook material 221c engages the outer surface of retainer 218 or strap 220b to securely fasten the retainer to the brace, as shown in FIG. 13C. Strap 220b has a similar construction as strap 220a with a first end joined to the retainer 218 and a second end with hook material 221d (FIG. 13A) attached thereto. A portion of strap 220b is received by a loop 222b that is joined to brace 202. The strap 220b folds back over itself such that the hook material 221d engages the outer surface of retainer 218 or strap 220a to securely fasten the retainer to the brace, as shown in FIG. 13C.

Two pockets 226a and 226b (FIGS. 13A and 13C) are stitched to the outer surface of brace 202. The pockets 226a and 226b receive ends 228a and 228b respectively of retainer 218 when the retainer is installed on the brace. As shown in FIG. 14, retainer 218 has hook material 230a and 230b joined to its outer surface. The hook material engages the outer surface of brace 202 when the ends 228a and 228b of the retainer are received by pockets 226a and 226b in the manner shown in FIG. 13C. Thus, the hook material 230a and 230b, pockets 226a and 226b, and straps 220a and 220b removably secure retainer 218 to brace 202.

Figure 15:
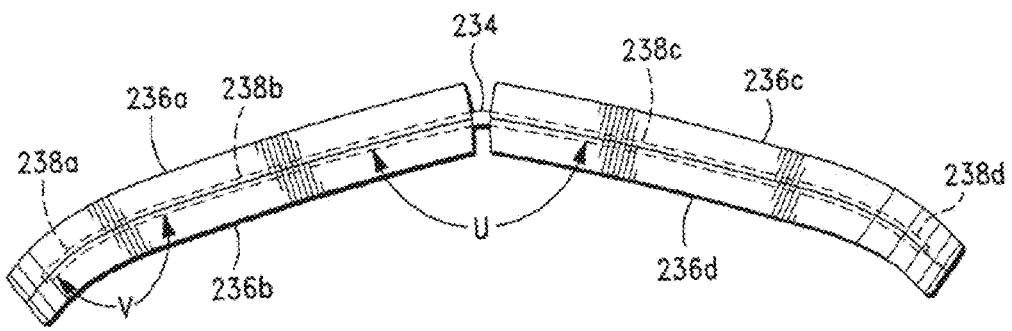
FIG. 15 is a side elevational view of the stiffener of the orthosis of FIG. 12.

As shown in FIG. 14, retainer 218 has an interior cavity 232 that is sized to receive a flexible stiffener 234 and sheets 236a, 236b, 236c, and 236d, shown in FIG. 15, which encase the stiffener. Sheets 236a-d are preferably formed from a soft resilient foam material for comfort. However, any type of material may be used to make the sheets. Further, it is within the scope of the invention for the stiffener 234 not to be encased with sheets.

Stiffener 234 comprises integrally formed sections 238a, 238b, 238c, and 238d. Sections 238a and 238b in combination comprise an upper end of the stiffener, and sections 238c and 238d in combination comprise a lower end of the stiffener. Sections 238b and 238c are joined such that there is an angle of U degrees between the sections. Angle U is preferably between 130 to 170 degrees when the stiffener is not flexed, and most preferably is approximately 150 degrees. There is also an angle of V degrees between sections 238a and 238b, and between sections 238c and 238d. Preferably, angle V is between 130 to 170 degrees when the stiffener is not flexed, and most preferably is approximately 150 degrees. The values for these angles are preferably chosen in order to shape the stiffener 234 so that it conforms to the medial side of arm 204 when the arm is at rest. The stiffener 234 is preferably formed from one of the materials described above with respect to the stiffener 14 shown in FIGS. 5 and 6 such that stiffener 234 is elastic and rebounds to its original form after flexing due to movement of the elbow.

As shown in FIG. 12, retainer 218 is coupled to brace 202 on the medial side of arm 204. The retainer 218 retains stiffener 234 such that the stiffener extends from the medial upper arm 204a to the medial forearm 204b for impeding movement of the elbow. Sections 238a and 238b of stiffener 234 are positioned adjacent to upper arm 204a, while sections 238c and 238d are positioned adjacent to forearm 204b. The region of stiffener 234 where sections 238b and 238c meet is positioned generally adjacent to the elbow (not shown).

Stiffener 234 is elastic such that it rebounds to its original form after flexing due to movement of the elbow caused by muscle contraction. The stiffener is made of a dynamic flexible material that resists flexing to impede movement of the elbow, but allows some movement in the joint. Referring to FIG. 12, the stiffener 234 is positioned in a first configuration EE. When the patient's muscle contraction causes a force B to be applied to the sections 238c and 238d of the stiffener 234, the stiffener is dynamically positioned in a second configuration FF, such that the sections 238c and 238d of the stiffener exhibit an angular displacement of Z degrees. The amount of angular displacement Z due to force B decreases the amount of angle U between sections 238b and 238c, which is shown in FIG. 15. When the force B is released from sections 238c and 238d the stiffener returns to its first configuration EE such that the angular displacement Z returns to zero and the angle U between sections 238b and 238c returns to its original value before the force B was applied to the stiffener. When the orthosis and stiffener are in use, it should be appreciated to those skilled in the art that movement of the elbow will exert a pressure across the various parts of the stiffener and not a force that is located at a single location. However, a resultant force at a particular location can be calculated based on the pressure distribution across the stiffener. The force B shown in FIG. 12 represents a resultant force that can be calculated based on a typical pressure or force distribution across the stiffener caused by movement of the elbow. Preferably, when force B is approximately 20 pounds the angle Z is between 20 to 60 degrees. It should be understood, however, that the material properties and dimensions of the stiffener may be altered so that the stiffener has any desired range of movement for a typical force exerted on it by any given patient.

Elbow movement causes the stiffener 234 to flex at approximately the location where sections 238b and 238c of the stiffener meet. As discussed above with respect to the hand orthosis of the first embodiment, it should be appreciated that the amount of angular displacement Z for a given force B depends on the thickness of the stiffener at the location where it flexes, the width of the stiffener at the location where it flexes, the distance between where the stiffener flexes and the location of the resultant force B, and the properties of the material that the stiffener is made from. While the distance between where the stiffener flexes and the resultant force B can vary based on the size of the user's forearm 204b, preferably this distance is between approximately 2 to 5 inches, and most preferably between approximately 2.5 to 4 inches. Preferably, the width of the stiffener at the location where sections 238b and 238c meet is between approximately 1.5 to 3.5 inches, and most preferably is approximately 2.5 inches. Preferably, the thickness of the stiffener is between approximately 0.002 to 0.07 inches, more preferably between approximately 0.005 to 0.04 inches, and most preferably between approximately 0.008 to 0.025 inches.

Fourth Embodiment

Knee Orthosis

Figure 16:
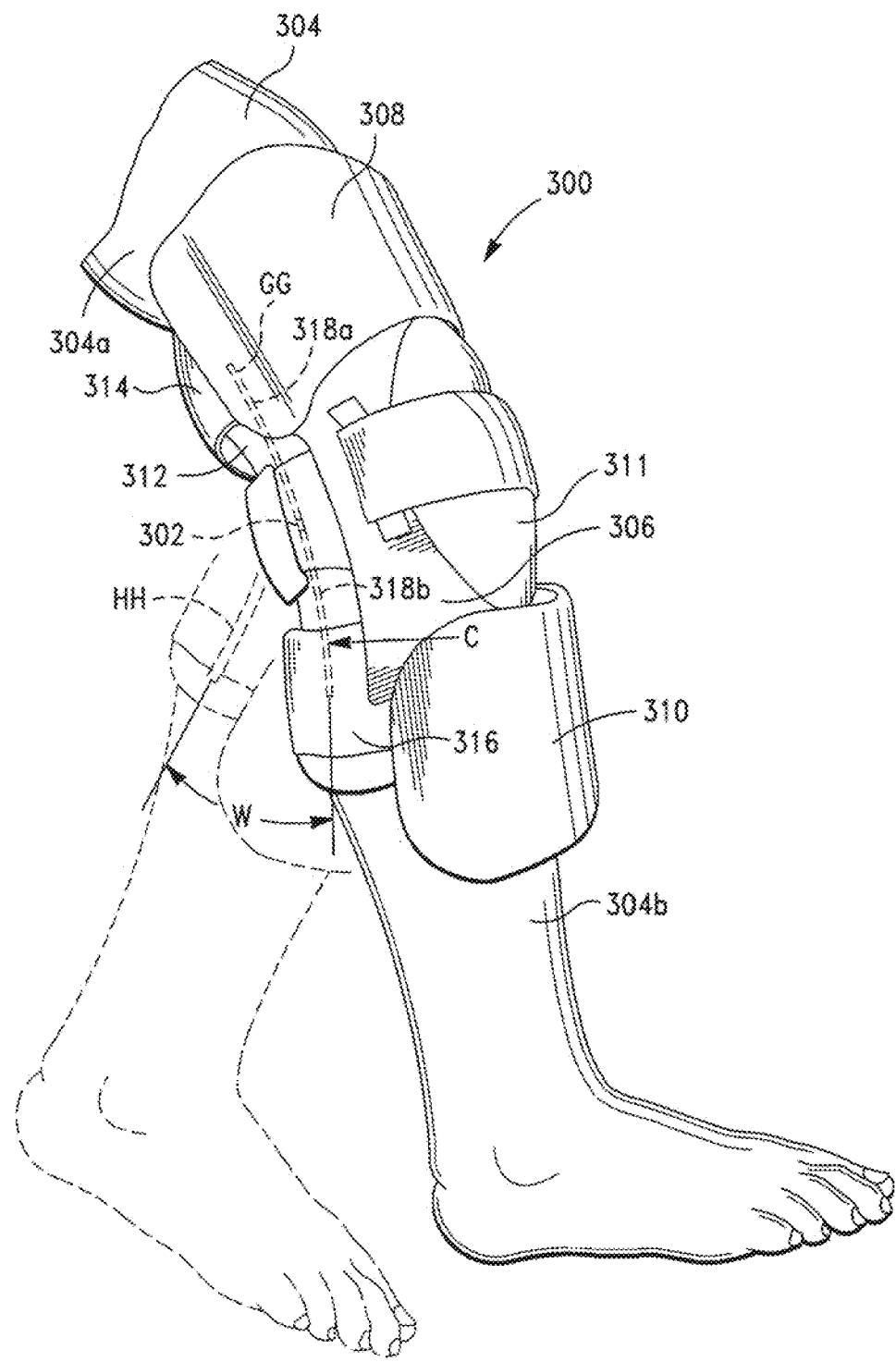
FIG. 16 is a perspective view of a knee orthosis according to an alternative embodiment of the present invention showing the orthosis in a flexed position in dashed lines.

Referring now to FIG. 16, a knee orthosis according to an alternative embodiment of the present invention is shown generally as 300. The knee orthosis is substantially similar to the elbow orthosis 200 shown in FIGS. 12-15 except that the knee orthosis is slightly larger so that it can receive a leg 304 and impede movement of a knee (not shown). Knee orthosis 300, like elbow orthosis 200, has a tubular brace 306. The brace 306 receives leg 304 and extends from an upper leg 304a to a lower leg 304b. Adjustable straps 308 and 310 secure the brace to the leg via hook and loop fasteners (not shown) that are positioned in the same locations as the hook and loop fasteners 208a, 208b, 209a and 209b on the straps 206a and 206b of the elbow orthosis 200, shown in FIG. 12. The knee orthosis 300 also has hook and loop fasteners (not shown) positioned in the same locations as the hook and loop fasteners 203a, 203b. 205a and 205b of the elbow orthosis 200, shown in FIGS. 13B and 13C. The knee orthosis 300 additionally has a cap 311 which is secured to the brace with straps and hook and loop fasteners in the same manner as described above with respect to the cap 210 of elbow orthosis 200.

A retainer 312 is removably coupled to the brace 306 on the posterior side of the leg via straps (not shown) that are received by loops (not shown) attached to the brace in a similar manner as the retainer 218 of elbow orthosis 200 shown in FIG. 13. The retainer 312 is also removably coupled to the brace via pockets 314 and 316 attached to the brace and hook and loop fasteners (not shown) in the same manner as retainer 218 of elbow orthosis 200. The retainer is configured to retain a stiffener 302, shown in dashed lines, such that the stiffener extends across the knee (not shown) from the posterior upper leg 304a to the posterior lower leg 304b for impeding movement of the knee. The stiffener 302 preferably has a similar shape as the stiffener described above in connection with the elbow orthosis 200 such that the stiffener 302 conforms to the posterior side of leg 304. The stiffener 302 also is preferably constructed of one of the materials described above with respect to stiffener 14 shown in FIGS. 5 and 6. The stiffener comprises an upper end 318a adjacent to the upper leg 304a and a lower end 318b adjacent to the lower leg 304b.

Stiffener 302 is elastic such that it rebounds to its original form after movement of the knee caused by muscle contraction. The stiffener is made of a dynamic flexible material that resists flexing to impede movement of the knee, but allows some movement in the joint. Referring to FIG. 16, the stiffener 302 is positioned in a first configuration GG. When the patient's muscle contraction causes a force C to be applied to the lower end 318b of the stiffener 302, the stiffener is dynamically positioned in a second configuration HH, such that the lower end 318b exhibits an angular displacement of W degrees. When the orthosis and stiffener are in use, it should be appreciated to those skilled in the art that movement of the knee will exert a pressure across the various parts of the stiffener and not a force that is located at a single location. However, a resultant force at a particular location can be calculated based on the pressure distribution across the stiffener. The force C shown in FIG. 16 represents a resultant force that can be calculated based on a typical pressure or force distribution across the stiffener caused by movement of the knee. Preferably, when force C is approximately 20 pounds the angle W is between 20 to 60 degrees. It should be understood, however, that the material properties and dimensions of the stiffener may be altered so that the stiffener has any desired range of movement for a typical force exerted on it by any given patient.

Knee movement causes the stiffener 302 to flex at approximately the location where upper and lower ends 318a and 318b meet. As discussed above with respect to the hand orthosis of the first embodiment, it should be appreciated that the amount of angular displacement W for a given force C depends on the thickness of the stiffener at the location where it flexes, the width of the stiffener at the location where it flexes, the distance between where the stiffener flexes and the location of the resultant force C, and the properties of the material that the stiffener is made from. While the distance between where the stiffener flexes and the resultant force C can vary based on the size of the user's lower leg 304b, preferably this distance is between approximately 3.5 to 6.5, and most preferably is approximately 4.5 to 6 inches. Preferably, the width of the stiffener at the location where upper and lower ends 318a and 318b meet is between approximately 1.5 to 3.5 inches, and most preferably is approximately 2.5 inches. Preferably, the thickness of the stiffener is between approximately 0.002 to 0.07 inches, more preferably between approximately 0.005 to 0.04 inches, and most preferably between approximately 0.008 to 0.025 inches.

In operation, the orthosis 10 shown in FIGS. 1-7 is secured to a wrist 21 and hand 20 using wrist strap 18 and hand straps 22 and 24. To secure the orthosis to the wrist and hand the hook material 18a, 24a, and 32a-b (FIG. 3B) on each of straps 18, 22, and 24 is preferably first disengaged from attachment with loop material 34a, 34b, and 34c, shown in FIG. 3C, or the outer surface of cover 12, whichever they are attached to. The hand 20 and wrist 21 are then positioned over the orthosis such that the fingers 30a-30d are positioned over the finger portion 52 of the stiffener 14 shown in FIG. 7, the thumb 30e rests on the outside of hand stabilizer section 62a, the palm is positioned over the palm portion 50, and the forearm 27 is positioned inside the C-shaped channel formed by the forearm stabilizers 56 and 58. Three of the fingers 30a-30c may be inserted into the loops 29a-29c of the finger retainer 28, however, this step is optional. The straps 18, 22, and 24 are then wrapped over the hand and wrist as shown in FIGS. 1 and 2, and the hook material 18a, 24a, and 32a-b is engaged with loop material 34a, 34b, and 34c to secure the hand and wrist to the orthosis.

With the hand and wrist secured to the orthosis the stiffener 14 positioned inside cover 12 impedes flexion of the wrist 21 and fingers 30a-30d. If the stiffener flexes from first configuration AA to second configuration BB (FIG. 7) due to flexion of the wrist and/or fingers, the stiffener rebounds to the first configuration AA after flexion of the wrist and/or fingers subsides. When the stiffener flexes due to wrist and/or finger movement, it typically flexes at approximately the wrist end 48 of midportion 44, shown in FIGS. 5 and 7, while the forearm end 46 of the midportion remains stationary adjacent to forearm 27. Forearm stabilizers 56 and 58 are plastically deformable so that they may be bent upward into any desired position for retaining the forearm 27 within the channel formed by the stabilizers. Likewise, hand stabilizer 62 is plastically deformable so that it may be bent upward into any desired position for retaining the hand 20. If a stiffener such as the one shown in FIG. 8 is used with the orthosis, then the thumb abductor 72 may be bent downward into any desired position for supporting the thumb, and the finger sections 76a-76d may flex independently of each other.

The foot orthosis 100 shown in FIGS. 9-11 is secured to lower leg 106 and foot 113 via a fabric boot as shown and described in U.S. Pat. No. 7,163,519 to Price et al. The foot orthosis 100 is secured to the lower leg and foot such that the first end 104 of the L-shaped splint 102 is positioned adjacent to the posterior lower leg 106 and the opposite heel end 108 is positioned underneath the heel 110. The toes 115 are positioned over stiffener 112 such that the second end 124 of the stiffener is generally adjacent the toes. With the orthosis secured to the foot and toes in this manner the stiffener impedes flexion of the toes 115 and/or ankle 109. If toe and/or ankle flexion occurs and flexes the stiffener from its first configuration CC to its second configuration DD (FIG. 10), the stiffener rebounds to its first configuration CC after the toe and/or ankle flexion subsides. When the stiffener flexes due to flexion of the toes and/or ankle, the stiffener typically flexes at approximately bends 126 and 128.

The elbow orthosis 200 shown in FIGS. 12-15 is secured to upper arm 204a and forearm 204b for impeding movement of the elbow (not shown). To secure the elbow orthosis to arm 204 the hook material 208a and 208b (FIG. 13B) on straps 206a and 206b is disengaged from attachment with the loop material 209a and 209b (FIG. 13C) joined to brace 202 or the outer surface of the brace. Likewise, the hook material 203a and 203b (FIG. 13B) is disengaged from loop material 205a and 205b (FIG. 13C). The arm 204 is then positioned within the tubular brace 202 such that the medial side of the elbow is positioned generally adjacent to hole 202a. The brace 202 is then wrapped around the arm 204 so that hook material 203a and 203b (FIG. 13B) engages loop material 205a and 205b (FIG. 13C). The straps 206a and 206b are then respectively wrapped over the upper arm 204a and forearm 204b and the hook material 208a and 208b on the straps is engaged with the loop material 209a and 209b on the brace or the outer surface of the brace to secure the arm to the brace. If cap 210 is not already secured to brace 202, then it is secured to the brace using straps 212a, 212b, 212c, and 212d in the manner described above. With the arm positioned inside the brace, stiffener 234 impedes bending of the elbow. If the elbow bends and flexes the stiffener 234 from its first configuration EE to its second configuration FF (FIG. 12), the stiffener rebounds to the first configuration EE when the force 13 subsides. When the stiffener flexes due to bending of the elbow, the stiffener flexes at approximately the location where sections 238b and 238c meet while sections 238a and 238b remain stationary adjacent upper arm 204a.

The knee orthosis 300 shown in FIG. 16 operates in generally the same manner as the elbow orthosis 200 described above. The adjustable straps 308 and 310 secure brace 306 to the upper and lower leg 304a and 304b. With the leg 304 positioned inside of brace 306, stiffener 302 impedes bending of the knee (not shown). If lower leg 304b moves relative to upper leg 304a and flexes the stiffener 302 from its first configuration GG to its second configuration HH, the stiffener rebounds to its first configuration GG when there is no longer any three imparted on the stiffener. The stiffener flexes at approximately the location where upper and lower ends 318a and 318b meet, while upper end 318a remains stationary adjacent upper leg 304a.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. An orthosis for treating an uncontrollably contracted knee joint adapted to be worn on a patient's leg in the region of said patient's uncontrollably contracted knee, comprising:
   a stiffener formed of a flat sheet of flexible and resilient material adapted to be disposed on a posterior side of said patient's knee having a position of repose that conforms to a first angle defined by said of said patient's knee when said patient's knee is not bent, said flat sheet of material having an inherent bias so that it bends from said first angle to a second angle when external force is applied and returns to said first angle when said external force is removed;
   a substantially tubular brace adapted to receive said patient's leg, said substantially tubular brace having an anterior extend adapted to overlie an anterior side of said patient's leg and to extend above and below said patient's knee, a posterior extent adapted to overlie said posterior side of said leg and to extend above and below said knee, a medial extent adapted to overlie a medial side of said leg and to extend above and below said knee, and a lateral extent adapted to overlie a lateral side of said leg and to extend above and below said knee, each of said extents of said substantially tubular brace having a common extent;
   a retainer coupled to said substantially tubular brace on said posterior extent and said retainer having an extent substantially equal to the extent of said posterior extent;
   said stiffener disposed within said retainer, said stiffener having an extent substantially equal to the extent of said retainer;
   said stiffener resisting bending of said knee from said first angle to said second angle;
   said stiffener bending from said first angle to said second angle when said patient's muscle is under contraction;
   said stiffener resisting but not preventing bending of said patient's knee when said patient's muscle is under said contraction;
   said stiffener returning to said first angle under said inherent bias after said contraction has terminated;
   said stiffener being bent at said first angle when selectively used with a patient having a knee which can be held in an unbent position so that an involuntary muscle contraction bends the knee and hence the stiffener from said first angle to said second angle, said stiffener returning to said first angle when such muscular contraction ends; and
   said stiffener having a bend formed therein when in its position of repose when selectively used with a patient having a knee that cannot be held comfortably in a straight, unbent position, said bend matching the bend in the patient's knee so that the stiffener is not displaced from its position of repose until said patient's muscles contract;
   said stiffener formed of tempered spring steel;
   said tempered spring steel having a Unified Numbering System identifier of G 10950;
   said tempered spring steel having a yield tensile strength of about 100 to 320 kilopounds per square inch;
   said stiffener having a modulus of elasticity of about 150 to 300 GPa;
   said stiffener having a thickness of about 0.008 to 0.07 inches;
   said stiffener being formed of heat treated and tempered steel including between approximately 0.9 to 1.05% carbon, and said steel having a hardness of about 45 to 60 on the Rockwell C scale;
   said stiffener having an upper end adapted to be positioned adjacent said upper leg and said stiffener having a lower end adapted to be positioned adjacent said lower leg;
   said lower end of said stiffener having an angular displacement of about 20 to 60 degrees when a force of 20 pounds is applied to said lower end of said stiffener.

* * * * *